United States Patent
Lazdunski et al.

(10) Patent No.: US 6,812,017 B2
(45) Date of Patent: Nov. 2, 2004

(54) MAMMALIAN SECRETED GROUP IIF PHOSPHOLIPASE A2

(75) Inventors: Michel Lazdunski, Nice (FR); Gérard Lambeau, Blausasc (FR); Emmanuel Valentin, Antibes (FR)

(73) Assignee: Centre National de la Recherche Scientique - CNRS (FR)

( * ) Notice: Subject to any disclaimer, the term of this patent is extended or adjusted under 35 U.S.C. 154(b) by 0 days.

(21) Appl. No.: 09/975,456

(22) Filed: Oct. 11, 2001

(65) Prior Publication Data

US 2003/0073087 A1 Apr. 17, 2003

Related U.S. Application Data

(60) Provisional application No. 60/239,491, filed on Oct. 11, 2000.

(51) Int. Cl.[7] .................................................. C12N 9/16
(52) U.S. Cl. ...................... 435/196; 435/198; 424/94.6; 536/23.2
(58) Field of Search ................................. 435/196, 198; 424/94.6; 536/23.2

(56) References Cited

FOREIGN PATENT DOCUMENTS

WO  WO 01/85956 A2 * 11/2001

OTHER PUBLICATIONS

Valentin et al. "Cloning and recombinant expression of human group IIF–secreted phospholipase A2" Biochem. Biophys. Res. Commu. 279, 223–228 (2000).*
Valentine et al. "On the diversity of secreted phospholipasees A2" J. Biol. Chem. 274, 31195–31202 (1999).*

* cited by examiner

Primary Examiner—Nashaat T. Nashed
(74) Attorney, Agent, or Firm—Piper Rudnick LLP (57) ABSTRACT

DNA and peptide sequences encoding a novel mammalian secreted group IIF phospholipase $A_2$ wherein said enzyme is $Ca^{2+}$-dependent, maximally active at pH 7–8, and hydrolyzes phosphatidylglycerol versus phosphatidylcholine with a 15-fold preference and more particularly, a novel human group IIF phospholipase $A_2$. The invention also concerns the use of this enzyme in methods for screening various chemical compounds.

2 Claims, 4 Drawing Sheets

Fig. 4

SEQUENCE LISTING

<160> NUMBER OF SEQ ID NOS: 10

<210> SEQ ID NO 1
<211> LENGTH: 507
<212> TYPE: DNA
<213> ORGANISM: Homo sapiens
<220> FEATURE:
<221> NAME/KEY: CDS
<222> LOCATION: (1)..(507)
<223> OTHER INFORMATION: cDNA encoding human group IIF secreted
      phospholipase A2

<400> SEQUENCE: 1

```
atg aag aag ttc ttc acc gtg gcc atc ctt gct ggc agc gtt ctg tcc      48
Met Lys Lys Phe Phe Thr Val Ala Ile Leu Ala Gly Ser Val Leu Ser
1               5                  10                  15 aca gct cac ggc agc ctg ctc aac ctg aag gcc atg gtg gag gcc gtc      96
Thr Ala His Gly Ser Leu Leu Asn Leu Lys Ala Met Val Glu Ala Val
            20                  25                  30 aca ggg agg agc gcc atc ctg tcc ttc gtg ggc tac ggt tgc tac tgt     144
Thr Gly Arg Ser Ala Ile Leu Ser Phe Val Gly Tyr Gly Cys Tyr Cys
```

-continued

```
                35                  40                  45
ggg ctg ggg ggc cgt ggc cag ccc aag gat gag gtg gac tgg tgc tgc    192
Gly Leu Gly Gly Arg Gly Gln Pro Lys Asp Glu Val Asp Trp Cys Cys
    50                  55                  60 cac gcc cac gac tgc tgc tac cag gaa ctc ttt gac caa ggc tgt cac    240
His Ala His Asp Cys Cys Tyr Gln Glu Leu Phe Asp Gln Gly Cys His
65                  70                  75                  80 ccc tat gtg gac cac tat gat cac acc atc gag aac aac act gag ata    288
Pro Tyr Val Asp His Tyr Asp His Thr Ile Glu Asn Asn Thr Glu Ile
                85                  90                  95 gtc tgc agt gac ctc aac aag aca gag tgt gac aag cag aca tgc atg    336
Val Cys Ser Asp Leu Asn Lys Thr Glu Cys Asp Lys Gln Thr Cys Met
            100                 105                 110 tgt gac aag aac atg gtt ctg tgc ctc atg aac cag acg tac cga gag    384
Cys Asp Lys Asn Met Val Leu Cys Leu Met Asn Gln Thr Tyr Arg Glu
        115                 120                 125 gag tac cgt ggc ttc ctc aat gtc tac tgc cag ggc ccc acg ccc aac    432
Glu Tyr Arg Gly Phe Leu Asn Val Tyr Cys Gln Gly Pro Thr Pro Asn
    130                 135                 140 tgc agc atc tat gaa ccg ccc cct gag gag gtc acc tgc agt cac caa    480
Cys Ser Ile Tyr Glu Pro Pro Pro Glu Glu Val Thr Cys Ser His Gln
145                 150                 155                 160 tcc cca gcg ccc ccc gcc cct ccc tag                                507
Ser Pro Ala Pro Pro Ala Pro Pro
                165
```

<210> SEQ ID NO 2
<211> LENGTH: 168
<212> TYPE: PRT
<213> ORGANISM: Homo sapiens

<400> SEQUENCE: 2

```
Met Lys Lys Phe Phe Thr Val Ala Ile Leu Ala Gly Ser Val Leu Ser
1               5                   10                  15

Thr Ala His Gly Ser Leu Leu Asn Leu Lys Ala Met Val Glu Ala Val
                20                  25                  30

Thr Gly Arg Ser Ala Ile Leu Ser Phe Val Gly Tyr Gly Cys Tyr Cys
            35                  40                  45

Gly Leu Gly Gly Arg Gly Gln Pro Lys Asp Glu Val Asp Trp Cys Cys
    50                  55                  60

His Ala His Asp Cys Cys Tyr Gln Glu Leu Phe Asp Gln Gly Cys His
65                  70                  75                  80

Pro Tyr Val Asp His Tyr Asp His Thr Ile Glu Asn Asn Thr Glu Ile
                85                  90                  95

Val Cys Ser Asp Leu Asn Lys Thr Glu Cys Asp Lys Gln Thr Cys Met
            100                 105                 110

Cys Asp Lys Asn Met Val Leu Cys Leu Met Asn Gln Thr Tyr Arg Glu
        115                 120                 125

Glu Tyr Arg Gly Phe Leu Asn Val Tyr Cys Gln Gly Pro Thr Pro Asn
    130                 135                 140

Cys Ser Ile Tyr Glu Pro Pro Pro Glu Glu Val Thr Cys Ser His Gln
145                 150                 155                 160

Ser Pro Ala Pro Pro Ala Pro Pro
                165
```

<210> SEQ ID NO 3
<211> LENGTH: 25
<212> TYPE: DNA

-continued

<213> ORGANISM: Artificial Sequence
<220> FEATURE:
<223> OTHER INFORMATION: Description of Artificial Sequence: Primer

<400> SEQUENCE: 3
atgaagaagt tcttcaccgt ggcca                                  25

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 4
accctcctcc cgctctctct ctcaaa                                 26

<210> SEQ ID NO 5
<211> LENGTH: 148
<212> TYPE: PRT
<213> ORGANISM: Homo sapiens

<400> SEQUENCE: 5

Met Lys Leu Leu Val Leu Ala Val Leu Leu Thr Val Ala Ala Ala Asp
 1               5                  10                  15

Ser Gly Ile Ser Pro Arg Ala Val Trp Gln Phe Arg Lys Met Ile Lys
            20                  25                  30

Cys Val Ile Pro Gly Ser Asp Pro Phe Leu Glu Tyr Asn Asn Tyr Gly
        35                  40                  45

Cys Tyr Cys Gly Leu Gly Gly Ser Gly Thr Pro Val Asp Glu Leu Asp
    50                  55                  60

Lys Cys Cys Gln Thr His Asp Asn Cys Tyr Asp Gln Ala Lys Lys Leu
65                  70                  75                  80

Asp Ser Cys Lys Phe Leu Leu Asp Asn Pro Tyr Thr His Thr Tyr Ser
                85                  90                  95

Tyr Ser Cys Ser Gly Ser Ala Ile Thr Cys Ser Ser Lys Asn Lys Glu
            100                 105                 110

Cys Glu Ala Phe Ile Cys Asn Cys Asp Arg Asn Ala Ala Ile Cys Phe
        115                 120                 125

Ser Lys Ala Pro Tyr Asn Lys Ala His Lys Asn Leu Asp Thr Lys Lys
    130                 135                 140

Tyr Cys Gln Ser
145

<210> SEQ ID NO 6
<211> LENGTH: 144
<212> TYPE: PRT
<213> ORGANISM: Homo sapiens

<400> SEQUENCE: 6

Met Lys Thr Leu Leu Leu Ala Val Ile Met Ile Phe Gly Leu Leu
 1               5                  10                  15

Gln Ala His Gly Asn Leu Val Asn Phe His Arg Met Ile Lys Leu Thr
            20                  25                  30

Thr Gly Lys Glu Ala Ala Leu Ser Tyr Gly Phe Tyr Gly Cys His Cys
        35                  40                  45

Gly Val Gly Gly Arg Gly Ser Pro Lys Asp Ala Thr Asp Arg Cys Cys
    50                  55                  60

Val Thr His Asp Cys Cys Tyr Lys Arg Leu Glu Lys Arg Gly Cys Gly

```
                65                  70                  75                  80
Thr Lys Phe Leu Ser Tyr Lys Phe Ser Asn Ser Gly Ser Arg Ile Thr
                        85                  90                  95

Cys Ala Lys Gln Asp Ser Cys Arg Ser Gln Leu Cys Glu Cys Asp Lys
                100                 105                 110

Ala Ala Ala Thr Cys Phe Ala Arg Asn Lys Thr Thr Tyr Asn Lys Lys
                115                 120                 125

Tyr Gln Tyr Tyr Ser Asn Lys His Cys Arg Gly Ser Thr Pro Arg Cys
                130                 135                 140

<210> SEQ ID NO 7
<211> LENGTH: 145
<212> TYPE: PRT
<213> ORGANISM: Homo sapiens

<400> SEQUENCE: 7

Met Glu Leu Ala Leu Leu Cys Gly Leu Val Met Ala Gly Val Ile
  1               5                  10                  15

Pro Ile Gln Gly Gly Ile Leu Asn Leu Asn Lys Met Val Lys Gln Val
                 20                  25                  30

Thr Gly Lys Met Pro Ile Leu Ser Tyr Trp Pro Tyr Gly Cys His Cys
                 35                  40                  45

Gly Leu Gly Gly Arg Gly Gln Pro Lys Asp Ala Thr Asp Trp Cys Cys
         50                  55                  60

Gln Thr His Asp Cys Cys Tyr Asp His Leu Lys Thr Gln Gly Cys Ser
 65                  70                  75                  80

Ile Tyr Lys Asp Tyr Tyr Arg Tyr Asn Phe Ser Gln Gly Asn Ile His
                 85                  90                  95

Cys Ser Asp Lys Gly Ser Trp Cys Glu Gln Gln Leu Cys Ala Cys Asp
                100                 105                 110

Lys Glu Val Ala Phe Cys Leu Lys Arg Asn Leu Asp Thr Tyr Gln Lys
                115                 120                 125

Arg Leu Arg Phe Tyr Trp Arg Pro His Cys Arg Gly Gln Thr Pro Gly
        130                 135                 140

Cys
145

<210> SEQ ID NO 8
<211> LENGTH: 154
<212> TYPE: PRT
<213> ORGANISM: Homo sapiens

<400> SEQUENCE: 8

Met Leu Leu Val His Leu Pro Ser Pro Gln Pro Gly Met Lys Ser Pro
  1               5                  10                  15

His Val Leu Val Phe Leu Cys Leu Leu Val Ala Leu Val Thr Gly Asn
                 20                  25                  30

Leu Val Gln Phe Gly Val Met Ile Glu Lys Met Thr Gly Lys Ser Ala
                 35                  40                  45

Leu Gln Tyr Asn Asp Tyr Gly Cys Tyr Cys Gly Ile Gly Gly Ser His
         50                  55                  60

Trp Pro Val Asp Gln Thr Asp Trp Cys Cys His Ala His Asp Cys Cys
 65                  70                  75                  80

Tyr Gly Arg Leu Glu Lys Leu Gly Cys Glu Pro Lys Leu Glu Lys Tyr
                 85                  90                  95

Leu Phe Ser Val Ser Glu Arg Gly Ile Phe Cys Ala Gly Arg Thr Thr
```

```
            100                 105                 110
Cys Gln Arg Leu Thr Cys Glu Cys Asp Lys Arg Ala Ala Leu Cys Phe
        115                 120                 125

Arg Arg Asn Leu Gly Thr Tyr Asn Arg Lys Tyr Ala His Tyr Pro Asn
130                 135                 140

Lys Leu Cys Thr Gly Pro Thr Pro Cys
145                 150

<210> SEQ ID NO 9
<211> LENGTH: 138
<212> TYPE: PRT
<213> ORGANISM: Homo sapiens

<400> SEQUENCE: 9

Met Lys Gly Leu Leu Pro Leu Ala Trp Phe Leu Ala Cys Ser Val Pro
  1               5                  10                  15

Ala Val Gln Gly Gly Leu Leu Asp Leu Lys Ser Met Ile Glu Lys Val
                 20                  25                  30

Thr Gly Lys Asn Ala Leu Thr Asn Tyr Gly Phe Tyr Gly Cys Tyr Cys
             35                  40                  45

Gly Trp Gly Gly Arg Gly Thr Pro Lys Asp Gly Thr Asp Trp Cys Cys
         50                  55                  60

Trp Ala His Asp His Cys Tyr Gly Arg Leu Glu Glu Lys Gly Cys Asn
 65                  70                  75                  80

Ile Arg Thr Gln Ser Tyr Lys Tyr Arg Phe Ala Trp Gly Val Val Thr
                 85                  90                  95

Cys Glu Pro Gly Pro Phe Cys His Val Asn Leu Cys Ala Cys Asp Arg
            100                 105                 110

Lys Leu Val Tyr Cys Leu Lys Arg Asn Leu Arg Ser Tyr Asn Pro Gln
        115                 120                 125

Tyr Gln Tyr Phe Pro Asn Ile Leu Cys Ser
130                 135

<210> SEQ ID NO 10
<211> LENGTH: 155
<212> TYPE: PRT
<213> ORGANISM: Homo sapiens

<400> SEQUENCE: 10

Met Leu Leu Leu Leu Pro Ser Leu Leu Leu Leu Leu Leu Leu Leu Pro
  1               5                  10                  15

Gly Pro Gly Ser Gly Glu Ala Ser Arg Ile Leu Arg Val His Arg Arg
                 20                  25                  30

Gly Ile Leu Glu Leu Ala Gly Thr Val Gly Cys Val Gly Pro Arg Thr
             35                  40                  45

Pro Ile Ala Tyr Met Lys Tyr Gly Cys Phe Cys Gly Leu Gly Gly His
         50                  55                  60

Gly Gln Pro Arg Asp Ala Ile Asp Trp Cys Cys His Gly His Asp Cys
 65                  70                  75                  80

Cys Tyr Thr Arg Ala Glu Glu Ala Gly Cys Ser Pro Lys Thr Glu Arg
                 85                  90                  95

Tyr Ser Trp Gln Cys Val Asn Gln Ser Val Leu Cys Gly Pro Ala Glu
            100                 105                 110

Asn Lys Cys Gln Glu Leu Leu Cys Lys Cys Asp Gln Glu Ile Ala Asn
        115                 120                 125

Cys Leu Ala Gln Thr Glu Tyr Asn Leu Lys Tyr Leu Phe Tyr Pro Gln
```

-continued

```
            130                 135                 140
Phe Leu Cys Glu Pro Asp Ser Pro Lys Cys Asp
145                 150                 155
```

MAMMALIAN SECRETED GROUP IIF PHOSPHOLIPASE A2

RELATED APPLICATION

This application claims priority of U.S. Provisional Application No. 60/239,491, filed Oct. 11, 2000. This earlier provisional application is hereby incorporated by reference.

FIELD OF THE INVENTION

This invention relates to DNA and peptide sequences encoding a novel mammalian secreted group IIF phospholipase $A_2$ and more particularly, a novel human group IIF phospholipase $A_2$. The invention also relates to the use of this enzyme in methods for screening various chemical compounds.

BACKGROUND

Phospholipases $A_2$ ($PLA_2$, EC 3.1.1.4.) form a superfamily of enzymes that catalyze the hydrolysis of glycerophospholipids at the sn-2 position, producing free fatty acids and lysophospholipids [1–4]. Many intracellular and secreted phospholipases $A_2$ ($sPLA_2s$) have been cloned in recent years [2,5], and several of them are involved in a variety of physiological and pathological functions including lipid digestion, cell proliferation, production of lipid mediators of inflammation, antibacterial defense, and cancer [4,6].

Within the phospholipase $A_2$ superfamily, $sPLA_2s$ form a relatively homogenous family of enzymes. They are characterized by the presence of several disulfides, an overall conserved three-dimensional structure and a common $Ca^{2+}$-dependent catalytic mechanism. Five novel mouse $sPLA_2s$ have been cloned during the last three years [7,8], and the mouse $sPLA_2$ family now comprises 8 distinct 14–16 kDa $sPLA_2s$ called group IB, IIA, IIC, IID, IIE, IIF, V and X, as well as otoconin-95, a $sPLA_2$-like protein with peculiar structural properties [9,10]. Interestingly, genes for group IIA, IIC, IID, IIE, IIF, and V $sPLA_2s$ all map to mouse chromosome 4, suggesting the existence of a $sPLA_2$ gene cluster on this chromosome [8]. Group IB, IIA, IID, IIE, V and X $sPLA_2s$, but not group IIF have been cloned from humans [11–13]. Conversely, group IIC $sPLA_2$ appears as a pseudogene in humans [14].

In addition, a novel human $sPLA_2$ with a predicted molecular mass of 55 kDA and a central domain similar to insect group III $sPLA_2s$ has recently been cloned [15], but it remains to be determined if this $sPLA_2$ is functional in the mouse species. This novel human $sPLA_2$ is also disclosed in the French International Patent Application N°01/59129. All mouse and human $sPLA_2s$ have distinct tissue distributions, suggesting that each of them exert non redundant functions that could be related to their different enzymatic properties [6,16,17], and/or their binding properties to specific receptors [17–19].

A comprehensive abbreviation system for the various $sPLA_2s$ is used thereafter: each $sPLA_2$ is abbreviated with a lowercase letter indicating the $sPLA_2$ species (m, h, for mouse and human, respectively) followed by capital characters identifying the $sPLA_2$ group (GI, GII, GIII, GV, and GX) and subgroup (A, B, C, D, E, F).

SUMMARY OF THE INVENTION

This invention relates to a mammalian secreted group IIF $sPLA_2$ which is $Ca^{2+}$-dependent, maximally active at pH of about 7–8, and hydrolyzes phosphatidylglycerol versus phosphatidylcholine with about a 15-fold preference.

BRIEF DESCRIPTION OF THE DRAWINGS

Other advantages and characteristics of the invention will become apparent by reading the following examples concerning the cloning, genomic organization, chromosomal mapping, tissue distribution, and the enzymatic properties of the recombinant hGIIF $sPLA_2$ and which refer to the attached drawings in which:

FIGS. 4A–4C represent the enzymatic properties of recombinant hGIIF $sPLA_2$.

DETAILED DESCRIPTION

This invention concerns the cloning, tissue distribution and recombinant expression in *E. coli* of a novel mammalian group IIF $sPLA_2$, more particularly, a novel human group IIF (hGIIF) $sPLA_2$. This group II $sPLA_2$ has unique structural features including a long, proline-rich C-terminal extension with an odd cysteine, and a very low pI value. It also has a specific tissue distribution and a fairly high propensity to hydrolyze POPC versus POPG as compared to the other $sPLA_2s$. Furthermore, using sequences generated by the Human Genome Project, the gene for hGIIF $sPLA_2$ maps to chromosome 1 together with 5 other $sPLA_2$ genes to form a $sPLA_2$ gene cluster that spans about 300 kilobase pair (kbp). Interestingly, 5 of these 6 genes code for group II enzymes and share relatively high level of identity. The last gene coding for group V $sPLA_2$ is, in fact, also related to group II $sPLA_2$ genes, as group V $sPLA_2$ does not contain a propeptide sequence and displays higher levels of identity to group II $sPLA_2s$ than to groups IB and X $sPLA_2s$. It is thus likely that these 6 different genes have arisen from recent and successive gene duplication events. It should be also noted that group IIA, IIC, IID, IIE and V sPLA$_2$s are all basic enzymes while group IIF is very acidic. On the other hand, group IB and X sPLA$_2$s appear more divergent in sequence and are located on different chromosomes [13]. Both contain a propeptide sequence and the group I specific disulfide bond between cysteines 11 and 77. Whether group IB, X or one of the group II-like sPLA$_2$s is more related to the sPLA$_2$ ancestor gene of the group I/II/V/X sPLA$_2$ collection [5] remains to be determined.

Thus, the invention concerns a novel mammalian secreted group IIF sPLA$_2$ wherein the enzyme is Ca$^{2+}$-dependent, maximally active at pH of about 7–8, and hydrolyzes phosphatidylglycerol versus phosphatidylcholine with a about 15-fold preference.

The invention concerns more particularly a mammalian secreted group IIF sPLA$_2$ constituted by or comprising the sequence of amino acids in the list of sequences under SEQ ID N°2. More particularly, the mammalian secreted group IIF sPLA$_2$ is a human secreted group IIF sPLA$_2$.

The invention concerns a nucleic acid molecule comprising or constituted of an encoding nucleic sequence for a mammalian secreted group IIF sPLA$_2$ or for a fragment of a mammalian secreted group IHF sPLA$_2$ whose amino acid sequence is represented under SEQ ID N°2. The invention relates more particularly to a nucleic acid molecule constituted by or comprising the sequence under SEQ ID N°1. The invention also concerns nucleotide sequences derived from the above sequence, for example, from the degeneracy of the genetic code or by the suppression or insertion of nucleotides (such as introns), and which encode for proteins presenting characteristics and properties of group IIF sPLA$_2$.

The invention also relates to polyclonal or monoclonal antibodies directed against one secreted group IIF sPLA$_2$ of the invention, a derivative or a fragment of these. These antibodies can be prepared by the methods described in the literature. According to prior art techniques, polyclonal antibodies are formed by the injection of proteins, extracted from animal tissues or produced by genetic transformation of a host, into animals, and then recuperation of antiserums and antibodies from the antiserums for example by affinity chromatography. The monoclonal antibodies can be produced by fusing myeloma cells with spleen cells from animals previously immunized using the proteins of the invention. These antibodies are useful in the search for new secreted mammalian group IIF sPLA$_2$ or the homologues of this enzyme in other mammals or again for studying the relationship between the secreted group IIF sPLA$_2$ of different individuals or species.

The invention also concerns a vector comprising at least one molecule of nucleic acid above, advantageously associated with adapted control sequences, together with a production or expression process in a cellular host of a mammalian group IIF sPLA$_2$ of the invention or a fragment thereof. The preparation of these vectors as well as the production or expression in a protein host of the invention can be carried out by molecular biology and genetic engineering techniques well known in the art.

An encoding nucleic acid molecule for a mammalian secreted group IIF sPLA$_2$ or a vector according to the invention can also be used to transform animals and establish a line of transgenic animals. The vector used is chosen in function of the host into which it is to be transferred; it can be any vector such as a plasmid. Thus, the invention also relates to cellular hosts expressing mammalian secreted group IIF sPLA$_2$ obtained in conformity with the preceding processes.

The invention also relates to nucleic and oligonucleotide probes prepared from the molecules of nucleic acid according to the invention. These probes, marked advantageously, are useful for hybridization detection of similar group IIF sPLA$_2$ in other individuals or species. According to prior art techniques, these probes are put into contact with a biological sample. Different hybridization techniques can be used, such as Dot-blot hybridization or replica hybridization (such as the Southern technique) or other techniques (such as DNA chips). Such probes constitute the tools making it possible to detect similar sequences quickly in the encoding genes for group IIF sPLA$_2$ which allow study of the presence, origin and preservation of these proteins. The oligonucleotide probes are useful for PCR experiments, for example, to search for genes in other species or with a diagnostic aim.

The secreted phospholipases A$_2$ (sPLA$_2$) are Ca$^{2+}$-dependent, disulfide-rich, 14–18 kDa enzymes that catalyze the hydrolysis of phospholipids at the sn-2 position to release fatty acids and lysophospholipids. sPLA$_2$s are also ligands that bind to a collection of soluble and membrane bound proteins which are likely to play a role in the biological functions of these enzymes. In the last few years, a number of structurally distinct mammalian sPLA$_2$s have been identified, and it has become clear that these sPLA$_2$s are expressed in a variety of tissues under both normal and pathological conditions (including inflammatory diseases, cancers, cardiac and brain ischemia, etc. . . . ), and are involved in a myriad of physiological and pathological roles. In mammalian cells stimulated with proinflammatory agonists, a subset of sPLA$_2$s play a role in the release of arachidonic acid for eicosanoid production. sPLA$_2$s are also involved in cell proliferation, cell migration, angiogenesis, cell contraction, apoptosis; neurosecretion, blood coagulation, adipogenesis, lipid metabolism (digestion, skin lipid barrier and lung surfactant formation, lipoprotein metabolism, etc. . . . ), spermatogenesis, fecondation, and embryogenesis. They also play a role in host defense and have antiviral and antibacterial properties against viruses like HIV-1 and various Gram-positive and Gram-negative bacterial strains. They also have antitumoral properties. They are also involved in various pathological conditions such as acute lung injury, acute respiratory distress syndrome, Crohn's disease, and various types of cancers where sPLA$_2$s can act as gene suppressors.

The invention concerns pharmaceutical compositions comprising as an active agent at least an encoding nucleic acid molecule for a mammalian secreted group IIF sPLA$_2$, or one molecule for a mammalian secreted group IIF sPLA$_2$ or a derivative of this protein. These pharmaceutical compositions can be used to treat or prevent viral and bacterial infections. They also can be used to treat or prevent cancers.

The invention is also useful in methods for identifying biologically active compounds with anti-inflammatory properties or more generally for identifying compounds that modulate sPLA$_2$ biological activities as listed above.

Such biologically active compounds can be identified by determining if a selected compound is capable of inhibiting the catalytic activity of sPLA$_2$ in cleaving a phospholipid to release fatty acids and lysophospholipids in a mixed micelle assay, a liposome assay, a system utilizing natural membranes, or in whole cells overexpressing this enzyme. A compound capable of inhibiting sPLA$_2$ catalytic activity may have anti-inflammatory or may behave as an antagonist of sPLA$_2$ in the sPLA$_2$ biological activities listed above.

For example, screening of compounds for potential anti-inflammatory activity can be performed with the novel sPLA$_2$ enzymes of this invention, purified to homogeneity from cell sources or produced recombinantly or synthetically. A selected compound may be added to a sPLA$_2$ enzyme of this invention in a mixed micelle assay, a liposome assay, or an assay system utilizing natural membranes and analyzed for inhibition of sPLA$_2$ activity. Alternatively, a selected compound may be added to whole cells which overexpress the sPLA$_2$ and the cells examined for inhibition of release of fatty acids or lysophospholipids. In this case, normal cells and cells overexpressing sPLA$_2$ can be cultured in labeled arachidonic acid. Signal is measured between the secreted products of both the normal and overexpressing cells to provide a baseline of sPLA$_2$ expression. A selected compound is then added to cultures and the cultures are grown in labeled arachidonic acid. If there is a difference in the signal (e.g., the amount of arachidonic acid produced) in the cells in the presence of the compound, this compound inhibits sPLA$_2$ activity and may be a potential anti-inflammatory compound.

Biologically active compounds can also be identified by screening the selected compounds for their binding properties to sPLA$_2$ receptors that bind group IIF sPLA$_2$s of this invention. These receptors include the family of N-type and M-type receptors which are likely to be involved in several biological activities of sPLA$_2$s including HIV-1 antiviral properties. For example, radioactively or fluorescently labeled sPLA$_2$s can be used in competition binding assays and selected compounds can be screened for inhibition of sPLA$_2$ binding.

Biologically active compounds can also be identified by screening the selected compounds for modulation of a sPLA$_2$ biological effect such as those listed above. For example, sPLA$_2$s of this invention may be added to cells in the presence or absence of a selected compound and cells may be assayed for cell proliferation, cell migration, cell contraction or apoptosis.

In general, another aspect of this invention is thus related to the use of a compound first identified by the methods described above. Novel pharmaceutical compositions may contain a therapeutically effective amount of a compound identified by an above method of this invention. These pharmaceutical compositions may be employed in methods for treating disease states or disorders involving group IIF sPLA$_2$s of this invention.

I. Materials and Methods.

I.1 Molecular Cloning of hGIIF sPLA$_2$.

Searching for sPLA$_2$s homologs in gene databases stored at the National Center for Biotechnology using the tBLASTn sequence alignment program [20] resulted in the identification of a human genomic sequence of 142849 nucleotides containing several regions of homology with mouse group IIF sPLA$_2$s. A set of oligonucleotides was designed from this genomic sequence (sense primer 5'-ATGAAGAAGTTCTTCACCGTGGCCA-3' (SEQ ID N°3 in the list of sequences in the appendix) and reverse primer 5'-ACCCTCCTCCCGCTCTCTCTCAAA-3' (SEQ ID N° 4 in the list of sequences in the appendix)) and used in RT-PCT experiments on different human cDNAs. A Dna product of the expected size was amplified from human cDNAs from spleen, heart, and fetal lung. Sequencing of the DNA fragments revealed complete identity with the genomic sequence after its appropriate splicing according to consensus exon-intron boundaries [21].

I.2 Tissue Distribution of Human sPLA$_2$s.

Multiple Tissue cDNA Panels (Clontech, catalog n° K1420-1 and K1421-1) were used as templates in RT-PCR experiments using primers specific for the human sPLA$_2$s cloned so far. PCR reactions were analyzed by agarose gel electrophoresis, transferred to positively charged nylon membranes, and hybridized with specific $^{32}$P-labeled internal oligonucleotide probes.

I.3 Recombinant Expression of hGIIF sPLA$_2$.

The preparation of a truncated GST hGIIF sPLA$_2$ construct, bacterial induction and preparation of sulfonated protein from inclusion bodies were carried out as previously described for mouse group IID sPLA$_2$ [7]. The hGIIF fusion protein was refolded by a rapid dilution method as follows. Sulfonated protein was dissolved to 10 mg/ml in 4 ml of 6 M guanidine-HCl, 50 mM Tris-HCl, pH 8.0, and added dropwise (~1 drop per second) to 2 liters of refolding buffer (50 mM Tris-HCl, pH 8.0, 0.9 M guanidine-HCl, 10 mM CaCl$_2$, 5 mM freshly added cysteine, 30% acetonitrile) with constant stirring at room temperature. Stirring was continued for a few minutes, and then the solution was allowed to sit without stirring at room temperature for ~2–3 days. The sPLA$_2$ enzymatic activity was monitored with the fluorimetric assay [16] until the activity increase starts to level off. After addition of 5 mM lauryl sulfobetaine (dodecyldimethyl-3-sulfopropylammonium, inner salt) and 1 mM methionine, the protein solution was concentrated by ultrafiltration to 50 ml with a YM-10 membrane (Amicon) and dialyzed 3 times against cleavage buffer (50 mM Tris-HCl, pH 8.0, 100 mM NaCl, 1 mM CaCl$_2$). Freshly made TPCK-treated trypsin (Sigma) was then added to a final concentration of 0.15 µg/ml, and the mixture was incubated overnight at room temperature, leading to a ~200-fold increase in sPLA$_2$ activity. The reaction mixture was directly loaded at 3 ml/min on a Vydac 218 TP1010 C18 reverse phase column equilibrated with solvent A (20% acetonitrile, 0.1% trifluoroacetic acid, 1 mM methionine). Elution was performed at 3 ml/min using a linear gradient (0–6.3% B over 2 min, followed by 6.3–27.5% B over 42 min) of solvent B (100% acetonitrile, 0.1% trifluoroacetic acid, 1 mM methionine). HPLC purified hGIIF sPLA$_2$ was neutralized with 2 M Tris base, 5 mM lauryl sulfobetaine was added and the sample was concentrated in a Centriprep-10 (Amicon). The protein was then dialyzed against 10 mM Tris pH 8.0, 0.1 mM DTT, at 4° C. for 1 cycle to cleave the disulfide between the cysteine in the C-terminal extension of the hGIIF sPLA$_2$ and free cysteine from the refolding buffer, and then against 10 mM Tris-HCl, pH 8.0 for two cycles. The approximate yield of final product per liter of E. coli culture is 3.7 mg. Concentrations of recombinant hGIIF sPLA$_2$ were determined by OD at 280 nm using an extinction coefficient of 10.37 calculated from the amino acid sequence.

I.4 sPLA$_2$ Catalytic Activity Studies.

The Ca$^{2+}$ and pH dependencies of hGIIF sPLA$_2$ were measured with POPC vesicles containing 1-palmitoyl-2-[1-$^3$H]palmitoyl-sn-glycero-3-phospho9choline vesicles and POPG vesicles containing 1-palmitoyl-2-[1-$^3$H]palmitoyl-sn-glycero-3-phosphoglyceril, respectively [7]. Substrate specificity studies were carried out using a slightly modified assay with the fatty acid binding protein [7]. Reaction mixtures contained 30 µM POPC, POPG, or POPS (1-Palmitoyl-2-Oleoyl-sn-Glcero-3-phosphoserine) large unicellular vesicles (0.1 µm, prepared by extrusion as described [222[) in Hanks' balanced salt solution with 1 mM Ca$^{2+}$, 1 mM Mg$^{2+}$, 9.7 µg fatty acid binding protein, and 1 µm 11-dansyl-undecanoic acid at 37° C. Assays were calibrated by adding a known amount of oleic acid to the complete assay in the absence of enzyme.

II. Results and Discussion.

II. Cloning of Human Group IIF sPLA$_2$.

Figure 1:
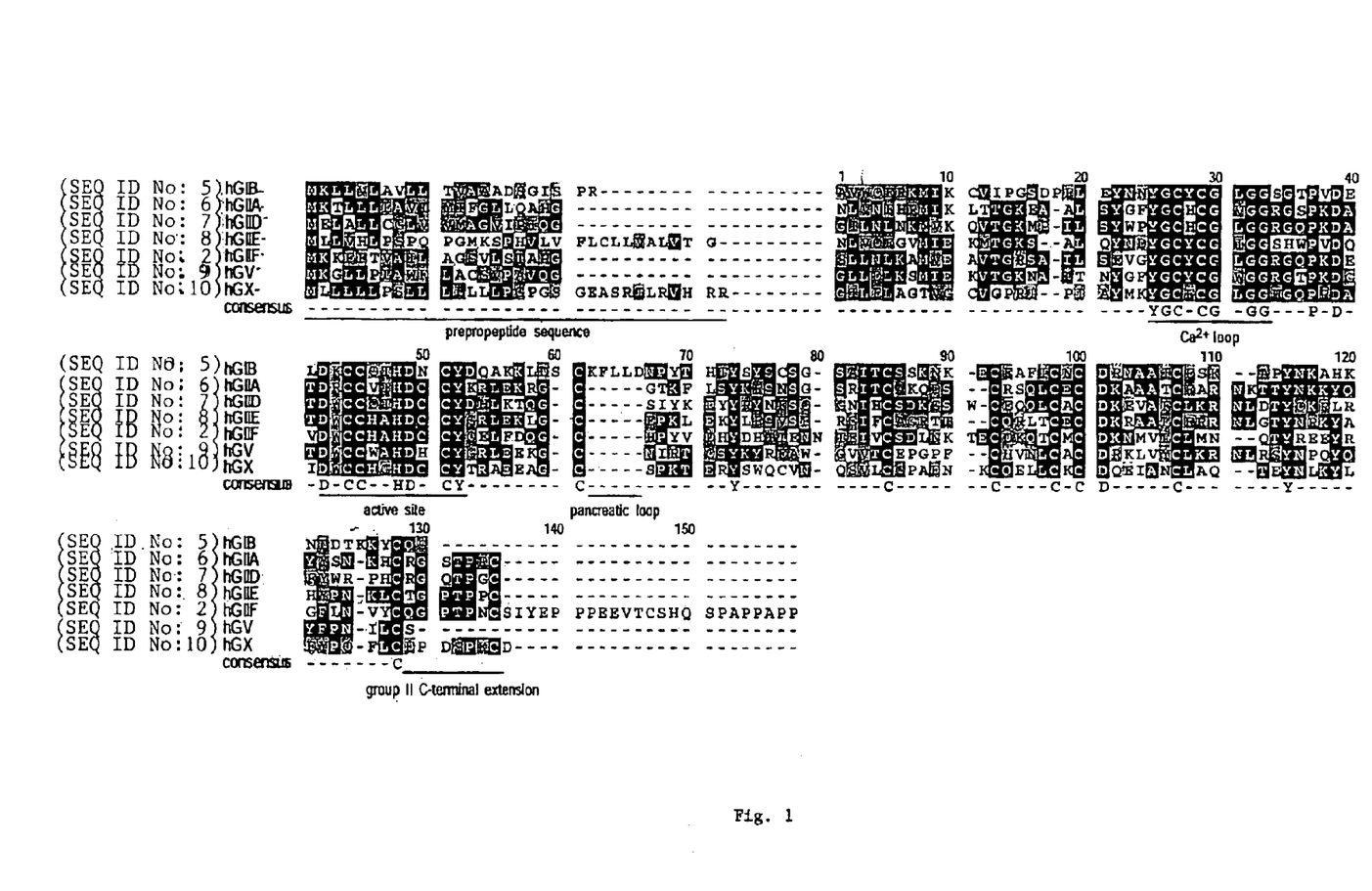
FIG. 1 represents the alignment of the amino acid sequences of human $sPLA_2s$. Sequences of full-length $sPLA_2$ proteins: hGIB (SEQ ID NO: 5), hGIIA (SEQ ID NO: 6), hGIID (SEQ ID NO: 7), hGIIE (SEQ ID NO: 8), hGIIF (SEQ ID NO: 2), hGV (SEQ ID NO: 9), and hGX (SEQ ID NO: 10) are shown. A consensus sequence for the 7 sequences of groups I/II/V/X human $sPLA_2s$ is presented.

Screening of nucleic sequence databases with various mouse sPLA$_2$s led to the identification of a large human genomic fragment of 142849 nucleotides with several regions of homology to mouse group hIF (mGIIF) sPLA$_2$ [8]. It was thus likely that this genomic clone contains a complete gene with several exons and introns coding for human group IIF sPLA$_2$. Based on homology with mGIIF, a set of sense and antisense primers was designed from the genomic sequence to amplify the full-length hGIIF sPLA$_2$ cDNA by RT-PCR. Human cDNAs from spleen, heart and fetal lung were used, and a strong amplification was obtained with spleen cDNA. The sequences of the amplified DNA fragments were found to contain an open reading frame of 168 amino acids comprising a signal peptide of 20 residues followed by a mature protein sequence of 148 residues (FIG. 1). This sequence is 74% identical to mGIIF sPLA$_2$ and contains all of the structural features of mGIIF, including the very long C-terminal extension of 23 amino acids [8]. Together, these results indicate that the 168 amino acid sequence corresponds to hGIIF sPLA$_2$ (FIG. 1).

The hGIIF mature protein sequence (calculated molecular mass 15,598 Da) is the most acidic sPLA$_2$ identified so far in mammals, with a calculated pI of 4.51. The 23 amino acid C-terminal extension of hGIIF also appears relatively acidic, as it contains 3 glutamic acid residues and no basic residues. Furthermore, one third (8 out 23) of the residues of this C-terminal extension are proline residues. Interestingly, these specific features appear to be conserved among species, as the mouse group IIF C-terminal sequence is also acidic and proline-rich. The odd cysteine residue found in the mGIIF sPLA$_2$ C-terminal extension is also conserved in the hGIIF sPLA$_2$ sequence. The possible involvement of these amino acids in the putative homo- or heterodimerization of group IIF sPLA$_2$s remains to be determined. Four potential N-glycosylation sites were found in the mature sequence of hGIIF SPLA$_2$ at positions 79, 89, 110 and 134 (FIG. 1) and only three of them (positions 79, 89 and 134) are conserved in the mGIIF sequence [8].

An alignment of the amino acid sequences of the 7 human catalytically-active group I/II/V/X sPLA$_2$ collection is presented in FIG. 1, and their respective levels of identity is shown in Table I. hGIIF sPLA$_2$ contains the different residues which are conserved in all catalytically active sPLA$_2$s and is particularly well-conserved with other human sPLA$_2$s in the Ca$^{2+}$ loop and the active site domains. hGIIF sPLA$_2$ however shows low levels of identity with other human sPLA$_2$s, and the most closely related sPLA$_2$ is hGIID with only 41% identity (Table I), indicating that hGIIF sPLA$_2$ is not an isoform of the previously cloned human sPLA$_2$s. It should be noted that the highest level of identity between any two sPLA$_2$s is observed between GIIA and GIIE (55% of identity in human species (Table I) and 51% in mouse species [8].

TABLE I

Level of amino acid sequence identity (%) between the different human sPLA$_2$s

| sPLA$_2$ | hGIIA | GIID | GIIE | hGIIF | hGV | hGX |
|---|---|---|---|---|---|---|
| hGIB | 35 | 36 | 35 | 27 | 30 | 29 |
| hGIIA |  | 50 | 55 | 33 | 44 | 35 |
| hGIID |  |  | 39 | 41 | 42 | 39 |
| hGIIE |  |  |  | 35 | 41 | 38 |
| hGIIF |  |  |  |  | 33 | 29 |
| hGV |  |  |  |  |  | 37 |

II.2 hGIIF sPLA$_2$ Gene Maps to Chromosome 1 and Belongs to a sPLAGene Cluster.

We have previously reported that the six genes for mGIIA, mGIIC, mGIID, mGIIE, mGIIF and mGV sPLA$_2$s are located in the distal part of mouse chromosome 4 and most likely form a sPLA$_2$ gene cluster [8]. Furthermore, the genes for hGIIA, hGIIC and hGV sPLA$_2$s have also been proposed to form a gene cluster positioned between the genetic markers AFM217zc3 and AFM290vb9 [14]. Here, we have taken advantage of the human genome sequencing project to show that the 6 corresponding human sPLA$_2$ genes are in fact located very close to each other within a DNA fragment of about 300 kbp. The organization of the sPLA$_2$ gene cluster is presented in FIG. 2.

Figure 2:
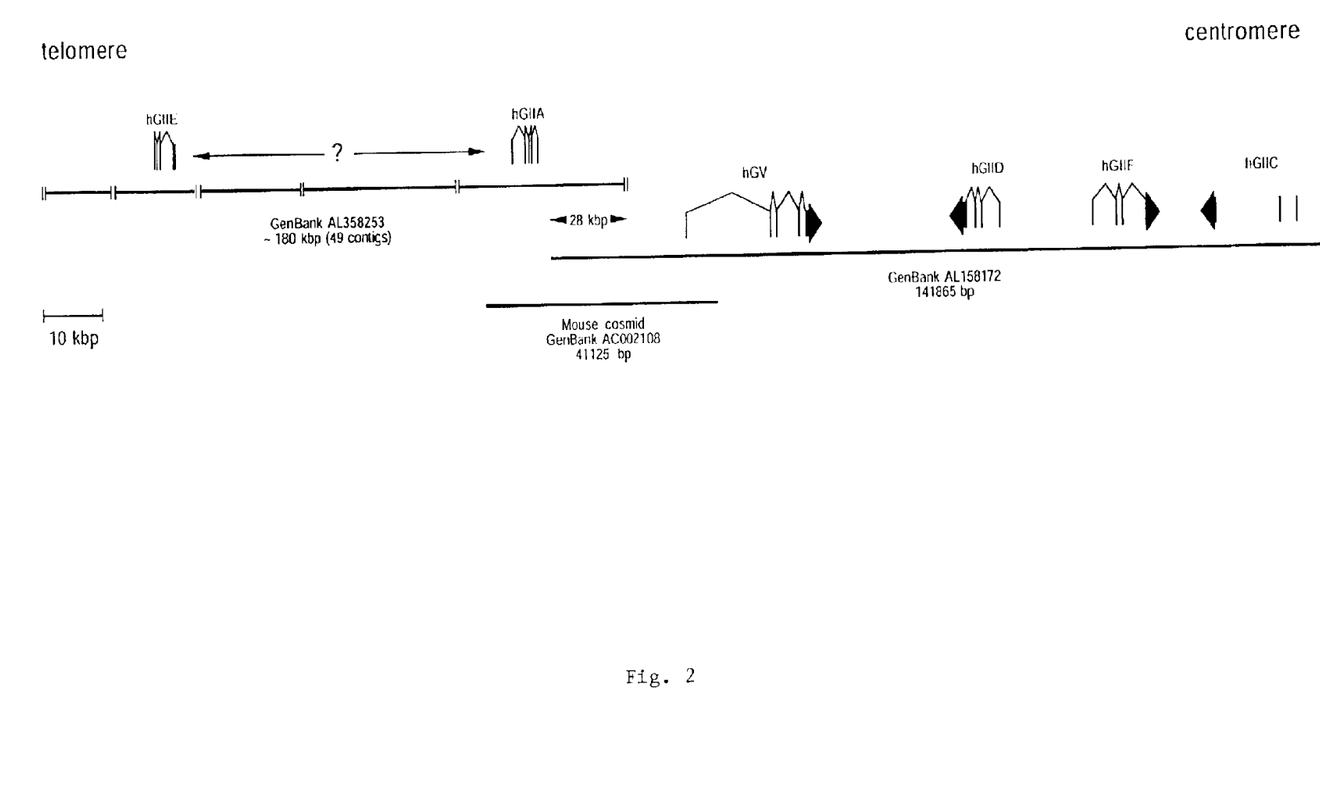
FIG. 2 represents a schematic diagram of the organization of the human chromosome 1p35 $sPLA_2s$ gene cluster. The total length between hGIIE gene and hGIIC pseudogene is about 300 kbp. The PAC clone GenBank n° AL358253 is not yet fully sequenced and the hatched bars indicate the different contigs of this PAC clone. The orientation and exon-intron boundaries of the different $sPLA_2s$ genes are schematically shown. The possible presence of 5' non coding exons in the hGIIC, hGIID, hGIIE and hGIIF genes are unknown, However, based on the sequence of the mouse cosmid KH1 that contains the mGIIA gene and a portion of the MGV gene, it is likely that the hGIIA and HGV genes are in a head to tail orientation and that the hGIIE gene is localized closer to the telomere.

The human PAC clone dJ169023 of 141,865 bp that contains the hGIIF gene was generated by the sequencing program of human chromosome 1, assigning the hGIIF gene to this chromosome. In addition to the hGIIF gene, this PAC clone contains also the full-length genes for HGV, HGIID, as well as the HGIIC pseudogene. The hGIIA and hGIIE genes were found to be localized on the overlapping PAC clone dJ169023 ion the telomeric direction (FIG. 2). At present, the available sequence of this PAC clone is composed of 49 unordered contigs of different lengths. Based on alignments of these different contigs with the sequence of the PAC clone AL158172, the overlapping sequence between AL158172 and AL358253 is estimated to be about 28 kbp. The relative orientation of hGIIA and HGIIE with the other sPLA$_2$ genes and the exact distances between hGIIA and hGIIE genes, and HGIIA and HGV genes are unknown. However, based on the full-length sequence of the mouse cosmid clone of 41,125 bp that contains the mGIIA gene and a portion of the mGV gene [23], it is likely that the hGIIA and hGV genes are organized in a head to tail orientation and that the hGIIE gene is localized in the telomeric direction, as presented in FIG. 2.

II.3 Analysis of the Tissue Distribution of hGIIF sPLA$_2$.

Figure 3:
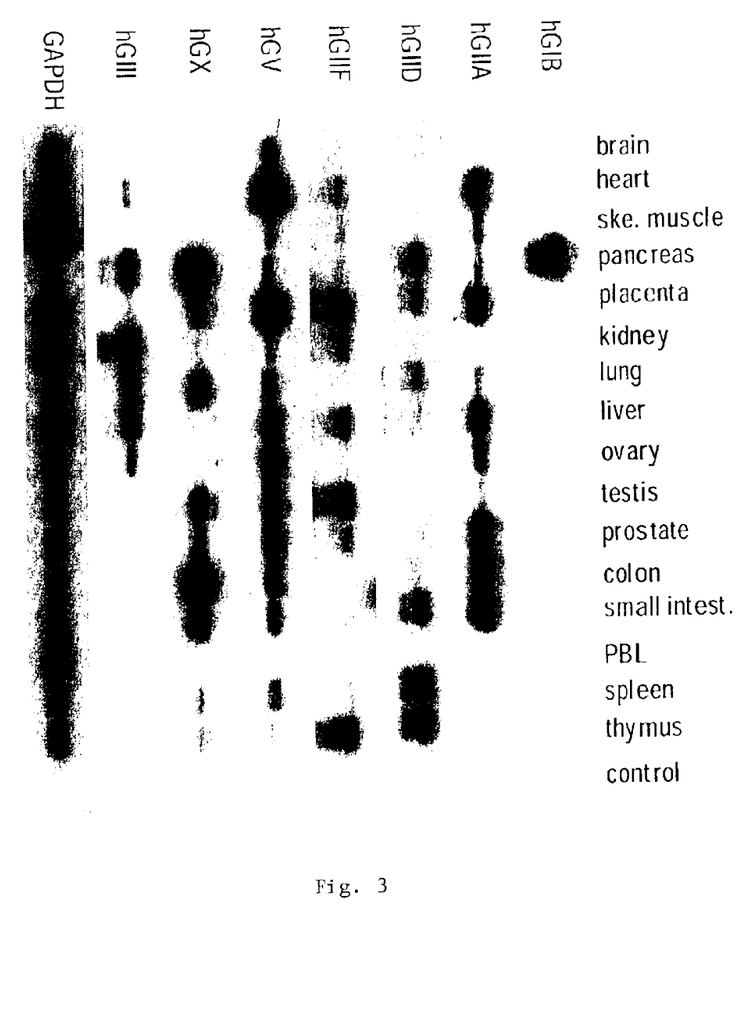
FIG. 3 represents the tissue distribution of the human $sPLA_2s$: hGIB (SEQ ID NO: 5), hGIIA (SEQ ID NO: 6), hGIID (SEQ ID NO: 7), hGIIF (SEQ ID NO: 2), hGV (SEQ ID NO: 9), hGX (SEQ ID NO: 10), hGIII, and GAPDH, as determined by RT-PCR on human adult cDNA panels. The amplified products were analyzed by Southern blot as described in materials and methods. No amplification was observed when cDNA was omitted in the PCR reaction (control lane).

The tissue distribution of hGIIF and other human sPLA$_2$s was analysed by RT-PCR experiments using commercial human cDNA panels. As shown in FIG. 3, hGIIF sPLA$_2$ is expressed at high levels in placenta, testis, thymus, and at lower levels in heart, kidney, liver and prostate. Very low signals were observed in skeletal muscle, pancreas, small intestine and spleen. In the mouse species, mGIIF transcripts were detected mostly in testis but also in several other tissues [8]. In the future, it will be interesting to analyse the expression of hGIIF sPLA$_2$ in embryos, since high levels of mGIIF transcripts were observed at different stages of embryonic development [8]. The different patterns of expression of human sPLA$_2$s presented in FIG. 3 and previously found for hGIIE sPLA$_2$ [11] clearly indicate that all human sPLA$_2$s including hGIIF most probably have non redundant functions. Overall, the tissue distributions of the human sPLA$_2$s resemble those previously found by northern-blot analysis [12,13,15]. Finally, it is interesting to note that all human sPLA$_2$s are expressed in the pancreas and that placenta, lung, colon and small intestine are also rich sources of sPLA$_2$.

II.4 Recombinant Expression of hGIIF sPLA$_2$.

In order to study the interfacial kinetic properties of hGIIF sPLA$_2$, we produced this enzyme as a recombinant fusion protein in *E. coli*. Inclusion bodies containing hGIIF fusion protein were solubilized and reduced, and free cysteines were sulfonated. Rapid dilution of the sulfonated protein into a buffer containing 30% acetonitrile, to minimize protein aggregation, produced refolded fusion protein which displayed maximal activity after 2–3 days. The fusion protein contains a factor Xa recognition site adjacent to the N-terminal residue of mature hGIIF which could be efficiently cleaved by using Factor Xa and trysin. Cleaved hGIIF sPLA$_2$ was purified to homogeneity by chromatography on a C18 reverse phase column, and the overall yield of purified hGIIF sPLA$_2$ is 3.7 mg per liter of *E. Coli* culture (data not shown).

Figure 4:
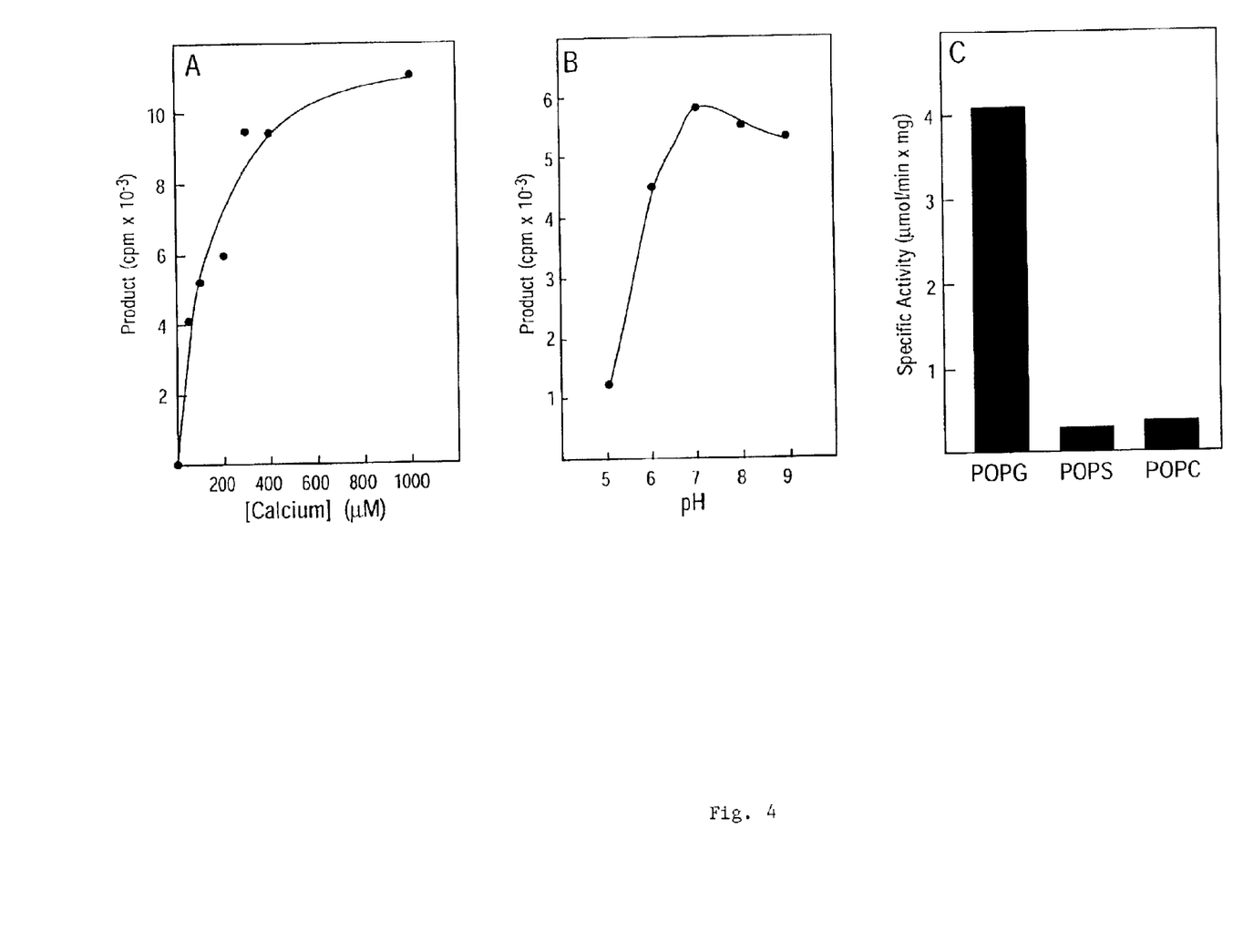
FIG. 4(A) shows $Ca^{2+}$-dependence of the hydrolysis of phosphatidylcholine vesicles.
FIG. 4(B) shows pH-dependence of the hydrolysis of phosphatidylglycerol vesicles.
FIG. 4(C) shows initial velocities for the hydrolysis of the indicated phospholipid vesicles. Full experimental details are provided in materials and methods.

The interfacial enzymatic properties of hGIIF sPLA$_2$ are summarized in FIG. 4. The hydrolysis of phospholipid vesicles by hGIIF sPLA$_2$ is strictly Ca$^{2+}$ dependent, as expected for a typical sPLA$_2$. Using PC vesicles as substrate, the enzyme displayed a hyperbolic dependence on the concentration of Ca$^{2+}$ (FIG. 4A), and an apparent $K_{Ca}^{2+}$ of 140±40 μM was calculated. FIG. 4B shows that the rate of hydrolysis of phosphatidylglycerol vesicles by hGIIF sPLA$_2$ increases with pH in the range 5–7, as expected from the deprotonation of the active site histidine residue, and then decreases slightly at pH above 7. The relative rates for the hydrolysis of POPG, POPS, and POPC vesicles by hGIIF sPLA$_2$ are compared in FIG. 4C. As for all mammalian sPLA$_2$S examined so far [7,8], the enzymatic activity of hGIIF sPLA$_2$ is highest with anionic POPG vesicles, which probably reflects the relatively high affinity of all sPLA$_2$s for POPG vesicles. Although hGIIF hydrolyzes POPC at only ~6% of the rate of POPG, this enzyme is much more active on POPC vesicles than hGIIA sPLA$_2$, which displays a greater than 10$^5$-fold preference for POPG versus POPC vesicles [8]. In this context, hGIIF appears more similar to hGV and hGX sPLA$_2$S, which are 3- and 10-fold more active on POPG versus POPC vesicles, respectively [16]. Whether exogenous hGIIF sPLA$_2$, like hGX sPLA$_2$, is able to efficiently release arachidonic acid from adherent cells will be interesting to analyse [16].

REFERENCES

Gelb, M. H., Jain, M. K., Hanel, A. M. and Berg, O. G. (1995) Annu. Rev. Biochem. 64, 653–688.
Balsinde, J., Balboa, M. A., Insel, P. A. and Dennis, E. A. (1999) Annu. Rev. Pharmacol. Toxicol. 39, 175–189.
Tischfield, J. A. (1997) J. Biol. Chem. 272, 17247–17250.
Lambeau, G. and Lazdunski, M. (1999) Trends Pharmacol. Sci. 20, 162–170.
Valentin, E. and Lambeau, G. (2000) Biochem. Biophys. Acta. in press.
Murakami, M., Nakatani, Y., Atsumi, G., Inoue, K. and Kudo, I. (1997) Crit. Rev. Immunol. 17, 225–283.
Valentin, E., Koduri, R. S., Scimeca, J. -C., Carle, G., Gelb, M. H., Lazdunski, M. and Lambeau, G. (1999) J. Biol. Chem. 274, 19152–19160.
Valentin, E., Ghomashchi, F., Gelb, M. H., Lazdunski, M. and Lambeau, G. (1999) J. Biol. Chem. 274, 31195–31202.
Verpy, E., Leibovici, M. and Petit, C. (1999) Proc. Natl. Acad. Sci. U S A 96, 529–534.
Wang, Y., Kowalski, P. E., Thalmann, I., Ornitz, D. M., Mager, D. L. and Thalmann, R. (1998) Proc. Natl. Acad. Sci. U S A 95, 15345–15350.
Suzuki, N. et al. (2000) J. Biol. Chem. 275, 5785–5793.
Ishizaki, J. et al. (1999) J. Biol. Chem. 274, 24973–24979.
Cupillard, L., Koumanov, K., Mattdi, M. G., Lazdunski, M. and Lambeau, G. (1997) J. Biol. Chem. 272, 15745–15752.
Tischfield, J. A. et al. (1996) Genomics 32, 328–333.
Valentin, E., Ghomashchi, F., Gelb, M. H., Lazdunski, M. and Lambeau, G. (2000) J. Biol. Chem. 275, 7492–7496.
Bezzine, S. et al. (2000) J. Biol. Chem. 275, 3179–3191.
Hanasaki, K. et al. (1999) J. Biol. Chem. 274, 34203–34211.
Hanasaki, K. and Arita, H. (1999) Arch. Biochem. Biophys. 372, 215–223.
Cupillard, L, Mulherkar, R., Gomez, N., Kadam, S., Valentin, E., Lazdunski, M. and Lambeau, G. (1999) J. Biol. Chem. 274, 7043–7051.
Altschul, S. F., Gish, W., Miller, W., Myers, E. W. and Lipman, D. J. (1990) J. Mol. Biol. 215, 403–410.
Guthrie, C. (1991) Science 253, 157–163.
Bayburt, T. and Gelb, M. H. (1997) Biochemistry 36, 3216–3231.
Cormier, R. T., Hong, K. H., Halberg, R. B., Hawkins, T. L., Richardson, P., Mulherkar, R., Dove, W. F. and Lander, E. S. (1997) Nat. Genet. 17, 88–91.

What is claimed is:

1. An isolated and purified human group IIF secreted phospholipase $A_2$ (sPLA2), which is $Ca^{2+}$-dependent, maximally active at pH of about 7–8, wherein said human secreted group IIF sPLA$_2$ consists of SEQ ID No: 2.

2. A composition comprising sPLA2 according to claim 1 and a pharmaceutical carrier.

* * * * *